US010058649B2

(12) United States Patent
Le Maner

(10) Patent No.: US 10,058,649 B2
(45) Date of Patent: Aug. 28, 2018

(54) DEVICE FOR PACKAGING A FLUID PRODUCT DISPENSER

(71) Applicant: APTAR FRANCE SAS, Le Neubourg (FR)

(72) Inventor: François Le Maner, La Vallee Montaure (FR)

(73) Assignee: APTAR FRANCE SAS, Le Neubourg (FR)

( * ) Notice: Subject to any disclaimer, the term of this patent is extended or adjusted under 35 U.S.C. 154(b) by 71 days.

(21) Appl. No.: 15/029,437

(22) PCT Filed: Oct. 13, 2014

(86) PCT No.: PCT/FR2014/052599
§ 371 (c)(1),
(2) Date: Apr. 14, 2016

(87) PCT Pub. No.: WO2015/055931
PCT Pub. Date: Apr. 23, 2015

(65) Prior Publication Data
US 2016/0271320 A1 Sep. 22, 2016

(30) Foreign Application Priority Data
Oct. 15, 2013 (FR) ...................................... 13 60012

(51) Int. Cl.
A61M 5/00 (2006.01)
A61M 5/20 (2006.01)
(Continued)

(52) U.S. Cl.
CPC .......... *A61M 5/002* (2013.01); *A61M 5/2053* (2013.01); *A61M 11/007* (2014.02);
(Continued)

(58) Field of Classification Search
CPC ................................................. B05B 11/0032
See application file for complete search history.

(56) References Cited

U.S. PATENT DOCUMENTS 2,084,540 A 6/1937 Smith
3,376,866 A 4/1968 Ogle
(Continued)

FOREIGN PATENT DOCUMENTS

JP 2004-208973 A 7/2004
JP 2011-93584 A 5/2011

OTHER PUBLICATIONS

International Search Report of PCT/FR2014/052599, dated Feb. 18, 2015. [PCT/ISA/210].
(Continued)

*Primary Examiner* — Bhisma Mehta
*Assistant Examiner* — Matthew A Engel
(74) *Attorney, Agent, or Firm* — Sughrue Mion, PLLC

(57) ABSTRACT

A packaging device for packaging a fluid dispenser (200), said dispenser comprising at least one reservoir (210) containing fluid, and a dispenser unit (220) that is actuated manually so as to dispense said fluid, said packaging device comprising a casing (100) that is provided with a base body (110) and with a cover (120) that is separable from said base body (110), starting from a closed position in which said dispenser (200) is packaged in said casing (100) and going to an open position in which said dispenser (200) may be removed from said casing (100), said casing (100) including at least one projection (130) that is adapted to co-operate with said dispenser (200) at least in the closed position of the cover (120), so as to block said dispenser unit (220) and prevent it from being actuated.

9 Claims, 2 Drawing Sheets

(51) Int. Cl.
*B05B 11/00* (2006.01)
*A61M 11/00* (2006.01)
*A61M 15/08* (2006.01)

(52) U.S. Cl.
CPC ...... *B05B 11/0032* (2013.01); *B05B 11/3059* (2013.01); *A61M 15/08* (2013.01); *A61M 2205/276* (2013.01); *A61M 2209/06* (2013.01)

(56) References Cited

U.S. PATENT DOCUMENTS

| | | | | |
|---|---|---|---|---|
| 3,767,085 A * | 10/1973 | Cannon | ................ | A61C 9/0026 222/137 |
| 4,909,791 A * | 3/1990 | Norelli | ................ | A61M 5/3216 604/192 |
| 5,566,828 A * | 10/1996 | Claes | ................ | A61M 5/003 206/1.5 |
| 6,364,866 B1 * | 4/2002 | Furr | ................ | A61M 5/1782 141/330 |
| 6,439,276 B1 * | 8/2002 | Wood | ................ | A61M 5/1782 141/27 |
| 6,708,846 B1 * | 3/2004 | Fuchs | ................ | A61M 11/06 222/327 |
| 8,123,719 B2 * | 2/2012 | Edwards | ................ | A61M 5/19 604/518 |
| 9,156,048 B2 * | 10/2015 | Le Maner | ................ | A61M 15/009 |
| 9,314,607 B2 * | 4/2016 | Barak | ................ | A61M 5/1417 |
| 2014/0000087 A1 * | 1/2014 | Le Maner | ................ | A61M 15/009 29/428 |
| 2014/0000587 A1 * | 1/2014 | Le Maner | ................ | A61M 15/009 128/200.14 |
| 2014/0001209 A1 * | 1/2014 | Le Maner | ................ | A61M 15/009 222/162 |
| 2016/0271320 A1 * | 9/2016 | Le Maner | ................ | A61M 11/007 |

OTHER PUBLICATIONS

Written Opinion of PCT/FR2014/052599, dated Feb. 18, 2015. [PCT/ISA/237].
International Preliminary Report on Patentability dated Apr. 21, 2016. in Application No. PCT/FR2014/052599.

* cited by examiner

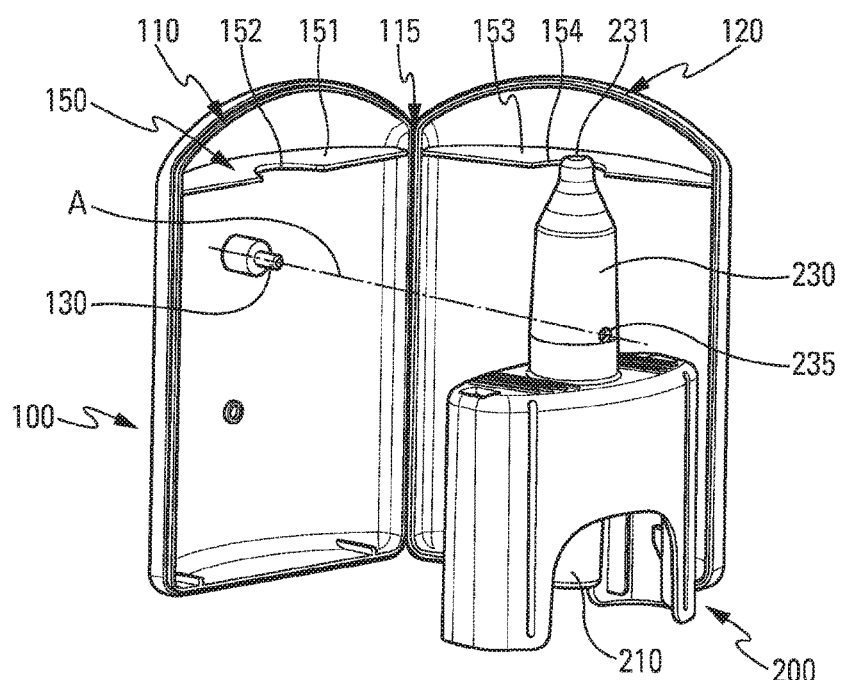
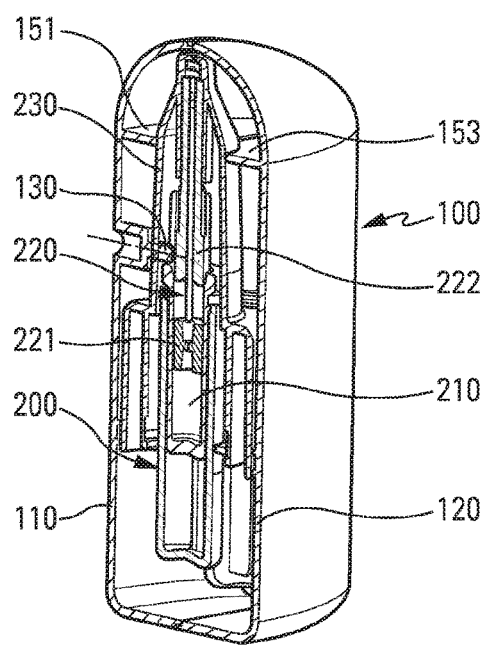
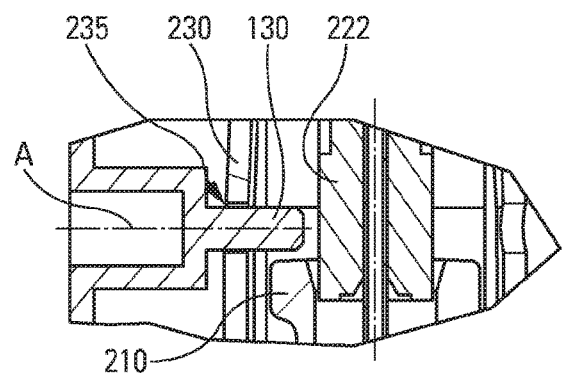
Fig. 1
Fig. 2
Fig. 3

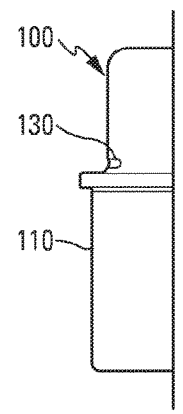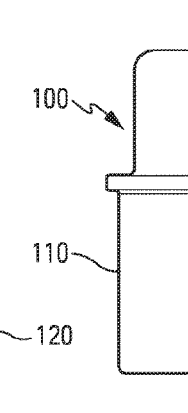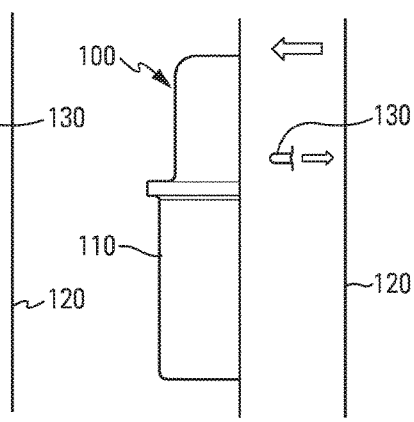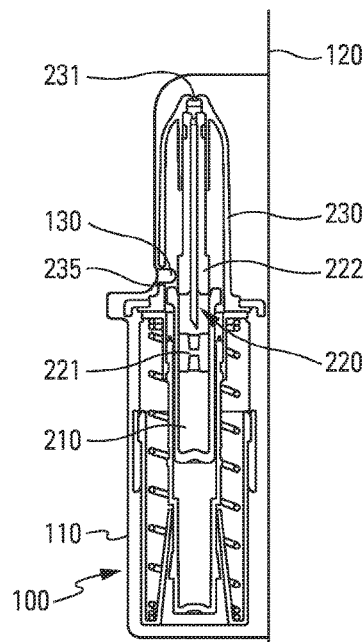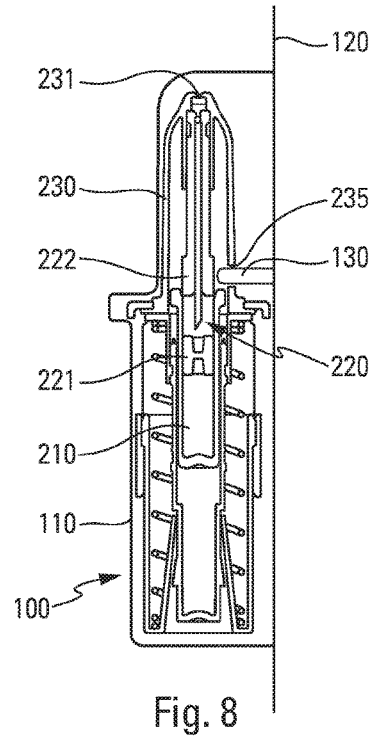

DEVICE FOR PACKAGING A FLUID PRODUCT DISPENSER

CROSS REFERENCE TO RELATED APPLICATIONS

This application is a National Stage of International Application No. PCT/FR2014/052599 filed Oct. 13, 2014, claiming priority based on French Patent Application No. 1360012, filed Oct. 15, 2013, the contents of all of which are incorporated herein by reference in their entirety.

The present invention relates to a packaging device for packaging a fluid dispenser.

Fluid dispensers are well known, in particular for dispensing pharmaceutical and cosmetic fluids, or fluids in the field of perfumery. Devices generally comprise at least one reservoir containing fluid, and a dispenser unit that is actuated manually so as to dispense said fluid. A problem that occurs with those devices relates to their safety during storage, while they are not being used. Thus, by way of example, the device being dropped may cause the dispenser unit to be actuated accidentally in full or in part. This may also occur immediately after assembling or filling the device. Such accidental full or partial actuation can pose significant problems, e.g. loss of a dose, loss of sealing, or subsequent malfunctioning of the device. Those problems are particularly harmful for dispenser devices of the single-dose or two-dose type for dispensing only one or two doses of fluid, and for devices of the autoinjector type.

Documents U.S. Pat. No. 3,376,866, JP 2004 208973, JP 2011 093584, and U.S. Pat. No. 2,084,540 describe prior-art devices.

An object of the present invention is to provide a packaging device for packaging a fluid dispenser for limiting or avoiding the above-mentioned drawbacks.

In particular, an object of the present invention is to provide such a device that avoids any risk of the dispenser being actuated accidentally in the event of the packaging device containing said dispenser being dropped.

The present invention thus provides an assembly comprising a packaging device for packaging a fluid dispenser together with said dispenser, said dispenser comprising at least one reservoir containing fluid, and a dispenser unit that is actuated manually so as to dispense said fluid, said packaging device comprising a casing that is provided with a base body and with a cover that is separable from said base body, starting from a closed position in which said dispenser is packaged in said casing and going to an open position in which said dispenser may be removed from said casing, said casing including at least one projection that is adapted to co-operate with said dispenser at least in the closed position of the cover, so as to block said dispenser unit and prevent it from being actuated, said dispenser including a body portion that is provided with at least one blocking opening that receives said projection, such that when said projection is arranged in said blocking opening, said projection prevents said dispenser unit from being actuated.

Advantageously, at least one of said at least one projection is arranged on the inside face of said base body.

Advantageously, at least one of said at least one projection is arranged on the inside face of said cover.

Advantageously, said dispenser includes a dispenser head that is provided with a dispenser orifice for dispensing the fluid, said dispenser unit being a pump or a metering valve that is actuated by moving said dispenser head relative to the reservoir, said at least one projection, in the closed position of the cover, preventing said movement of said dispenser head.

Advantageously, said dispenser head includes said blocking opening.

Advantageously, said dispenser unit includes a piston that is movable in a reservoir so as to expel the fluid out from said reservoir, and a piston rod that is connected to said piston during actuation, said piston being actuated by moving said piston rod relative to said reservoir, said at least one projection, in the closed position of the cover, preventing said movement of said piston rod relative to said reservoir.

Advantageously, said dispenser is an autoinjector.

Advantageously, said casing further includes positioner means for positioning the dispenser.

Advantageously, said positioner means comprise said at least one projection.

Advantageously, said cover is movable, in particular pivotable, relative to said base body, such that in the open position of said cover, said dispenser may be installed in and removed from said casing.

In a variant, said cover is fastened in tear-off manner to said base body.

These characteristics and advantages and others of the present invention appear more clearly from the following detailed description, given by way of non-limiting example, and with reference to the accompanying drawings, in which:

FIG. 1 is a diagrammatic perspective view of an advantageous embodiment of the packaging device, in its open position, with the dispenser in the process of being installed in the packaging device;

FIG. 2 is a diagrammatic perspective view in section on a vertical plane showing the FIG. 1 device in the closed position;

FIG. 3 is a view of a detail in vertical section;

FIG. 4, FIG. 5 and FIG. 6 are diagrammatic side views of three variants of another advantageous embodiment of the invention, with a casing in the form of a blister;

FIG. 7 is a diagrammatic section view of the FIG. 4 blister in its closed position, receiving a dispenser of the two-dose type; and FIG. 8 is a view, similar to the view in FIG. 7, of the FIG. 6 blister in its closed position, receiving a dispenser of the two-dose type.

In the present description, the term "fluid" comprises liquids, pastes, or powders, and the terms "top", "bottom", "vertical", and "horizontal" refer to the upright position of the device as shown in FIGS. 1 and 4.

FIG. 1, FIG. 2 and FIG. 3 show a first advantageous embodiment of the present invention, including a casing 100 forming part of a packaging device. In FIG. 1, the casing 100 is in its open position, with a dispenser 200 in the process of being installed.

The casing 100 comprises a base body 110 and a cover 120 that is movable, in particular pivotable, relative to said base body 110 between an open position in which said dispenser 200 may be installed in and removed from said casing 100, and a closed position in which said dispenser 200 is packaged in said casing 100. As shown in FIG. 1, the cover 120 may pivot about a side edge 115 of the base body 110, forming a hinge. The casing may be made as a single piece, with a film hinge forming the side pivot edge, or in two pieces, with a mechanical hinge between the base body and the cover.

The dispenser 200 may be of any type, e.g. a multi-dose device, i.e. a device comprising a pump or a valve as dispenser unit, mounted on a reservoir containing a plurality of doses. The dispenser may also be an injection device such as an autoinjector. In the embodiment shown in the figures, the dispenser 200 is a single-dose (or two-dose) dispenser, i.e. it contains only a single dose (or only two doses) of fluid to be dispensed. Naturally, this embodiment is not limiting.

In the embodiment shown, the dispenser 200 includes a reservoir 210 containing one or two doses of fluid to be dispensed. The dispenser 200 further includes a body portion 230 that is provided with at least one blocking opening 235. The body portion 230 is advantageously a dispenser head, as can be seen in FIGS. 1 and 2, provided with a dispenser orifice 231 for dispensing the fluid.

The dispenser unit 220 may be a pump or a metering valve that is actuated by moving said dispenser head 230 relative to the reservoir 210. In a variant, as can be seen in FIG. 2, said dispenser unit 220 may include a piston 221 that is movable in the reservoir 210 so as to expel the fluid out from said reservoir, and a piston rod 222 that is connected to said piston 221 during actuation, said piston 221 being actuated by moving said piston rod 222 relative to said reservoir 210.

In the invention, said casing 100 includes at least one projection 130 that is adapted to co-operate with said dispenser 200 at least in the closed position of the cover 120, so as to block said dispenser unit 220 and prevent it from being actuated.

Advantageously, as can be seen in FIG. 1, said at least one projection 130 is arranged on the inside face of said base body 110. In a variant, said at least one projection 130 may also be arranged on the inside face of said cover 120. If desirable, two projections 130 may be provided, one in the base body 110 and the other in the cover 120, in which event the dispenser 200 also includes two blocking openings 235.

In the embodiment in FIG. 1, the dispenser 200 is put into place in the casing 100, with a blocking opening 235 of the dispenser being engaged on a projection 130 provided in the base body 110, in the direction of the axis A shown in FIG. 1.

FIGS. 4 to 8 show another embodiment in which the casing 100 forms a blister for the dispenser 200, with the cover 120 fastened in tear-off manner to said base body 110. The base body may be made in the form of a thermoformed shell. The projection 130 may be formed integrally in the base body 110, as can be seen in FIGS. 4 and 7, or it may be formed on the cover 120, as can be seen in FIGS. 6 and 8. In both variants, the projection 130 may be formed directly in the base body or on the cover during their manufacture, or it may be formed separately and then bonded or clipped in the base body 110 as can be seen in FIG. 5, or on the cover 120 as can be seen in FIG. 6.

As can be seen in FIGS. 2, 3, 7, and 8, in its blocking position, the projection 130 extends inside the dispenser head 230 above the top edge of the reservoir 210, thereby preventing any relative movement between the reservoir 210 and the dispenser head 230.

Thus, in its blocking position, no actuation, not even in part, is possible while the projection 130 is in its blocking position, including if the packaging device is dropped.

Advantageously, said casing 100 may further include positioner means 150 for positioning the dispenser 200, in particular so as to avoid the dispenser dropping out while the casing is being opened. In particular, the positioner means 150 may comprise said at least one projection 130. In the embodiment in FIGS. 1 to 3, the positioner means may also include a positioner flange 151 that is formed in the base body 110, and a corresponding flange 153 that is formed in the cover 120. Each flange 151, 153 includes a central cutout 152, 154 that makes it possible to position said dispenser head 230. In the example in FIGS. 4 to 8, the positioner means may include a base body 110 having a shape that is adapted to the shape of the dispenser 200, said dispenser 200 thus being jammed in said base body even after the cover 120 has been torn off said base body.

Although the present invention is described above with reference to several particular embodiments, naturally the present invention is not limited by those embodiments, and, on the contrary, any useful modification could be applied thereto by the person skilled in the art, without going beyond the ambit of the present invention, as defined by the accompanying claims.

The invention claimed is:

1. An assembly comprising a packaging device for packaging a fluid dispenser (200), said dispenser comprising at least one reservoir (210) containing fluid, and a dispenser unit (220) that is actuated manually so as to dispense said fluid, said packaging device comprising a casing (100) that is provided with a base body (110) and with a cover (120) that is separable from said base body (110), starting from a closed position in which said dispenser (200) is packaged in said casing (100) and going to an open position in which said dispenser (200) may be removed from said casing (100), said casing (100) including at least one projection (130) that is adapted to co-operate with said dispenser (200) at least in the closed position of the cover (120), so as to block said dispenser unit (220) and prevent said dispenser unit from being actuated, wherein said dispenser (200) includes a body portion (230) that is provided with at least one blocking opening (235) that receives said at least one projection (130), such that when said at least one projection (130) is arranged in said at least one blocking opening (235), said at least one projection (130) prevents said dispenser unit (220) from being actuated, said at least one projection (130) being arranged on an inside face of said casing; and
wherein said dispenser includes a dispenser head that is provided with a dispenser orifice for dispensing the fluid, said dispenser unit being a pump or a metering valve that is actuated by moving said dispenser head relative to the at least one reservoir, said at least one projection, in the closed position of the cover, preventing said movement of said dispenser head.

2. The assembly according to claim 1, wherein said at least one projection (130) is arranged on an inside face of said base body (110).

3. The assembly according to claim 1, wherein said dispenser head (230) includes said at least one blocking opening (235).

4. The assembly according to claim 1, wherein said dispenser unit (220) includes a piston (221) that is movable in the at least one reservoir (210) so as to expel the fluid out from said at least one reservoir, and a piston rod (222) that is connected to said piston (221) during actuation, said piston (221) being actuated by moving said piston rod (222) relative to said at least one reservoir (210), said at least one projection (130), in the closed position of the cover (120), preventing said movement of said piston rod (222) relative to said at least one reservoir (210).

5. The assembly according to claim 4, wherein said dispenser is an autoinjector.

6. The assembly according to claim 1, wherein said casing (100) further includes a positioner means (150) for positioning the dispenser (200).

7. The assembly according to claim 1, wherein said cover (120) is pivotable relative to said base body (110), such that in the open position of said cover (120), said dispenser (200) may be installed in and removed from said casing (100).

8. The assembly according to claim 1, wherein said cover (120) is fastened in tear-off manner to said base body (110).

9. The assembly according to claim 1, wherein said at least one projection is arranged on an inside face of said cover.

\* \* \* \* \*